United States Patent
Petrov

(10) Patent No.: US 8,987,520 B2
(45) Date of Patent: Mar. 24, 2015

(54) FLUOROALKYL AND CHLOROFLUOROALKYL BENZENES

(71) Applicant: E I du Pont de Nemours and Company, Wilmington, DE (US)

(72) Inventor: Viacheslav A Petrov, Hockessin (DE)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 14/132,435

(22) Filed: Dec. 18, 2013

(65) Prior Publication Data

US 2014/0200372 A1  Jul. 17, 2014

Related U.S. Application Data

(60) Provisional application No. 61/751,388, filed on Jan. 11, 2013.

(51) Int. Cl.
*C07C 49/80* (2006.01)
*C07C 45/43* (2006.01)
*C07C 22/08* (2006.01)
*C07C 17/281* (2006.01)
*C07C 17/278* (2006.01)

(52) U.S. Cl.
CPC ............ *C07C 49/80* (2013.01); *C07C 17/281* (2013.01); *C07C 22/08* (2013.01); *C07C 45/43* (2013.01); *C07C 17/278* (2013.01)
USPC ............ 568/323; 568/335; 570/127; 570/144

(58) Field of Classification Search
USPC ............................. 568/323, 335; 570/127, 144
See application file for complete search history.

(56) References Cited

U.S. PATENT DOCUMENTS 5,157,171 A * 10/1992 Sievert et al. ................. 570/151
2012/0329837 A1* 12/2012 Booth ........................... 514/357

OTHER PUBLICATIONS

Gosselin et al. Unprecedented Catalytic Asymmetrica Reduction of N-H Imines. Organic Letters, 2005, vol. 7, No. 2, 355-358.*
Tanaka et al. A new entry for the oxidation of fluoroalkyl-substituted methanol derivatives: Scope and limitation of the organoiodine (V) reagent-catalyzed oxidation. Journal of Fluorine Chemistry, 2012, vol. 137, 99-104.*
Synthesis of Fluorinated Compounds, Monomers and Intermediates., Editors I. L. Knunaynts and G. G. Yakobson, Moscow, Chimiya (1977), pp. 141-142.
Christe et al., Relative Abilities of Fluorine and Chlorine to Stablize Carbenium Ions: Crystal Structures of Two Fluoro-Substituted Carbocatoins and of AS2F11, J. Am. Chem. Soc., vol. 122 (2000), pp. 481-487.
Creary, Reaction of Organometallic Reagents With Ethyl Trifluoroacetate and Diethyl Oxalate. Formation of Trifluoromethyl Ketones and α-Keto Esters Via Stable Tetrahedral Adducts, J. Org. Chem., vol. 52 (1987), pp. 5026-5030.
Gosselin et al., Unprecedented Catalytic Asymmetric Reduction of N-H Imines, Organic Letters, vol. 7, No. 2 (2005), pp. 355-358.
Petrov et al., New Hydrofluorocarbon (HFC) Solvents for Antimony Pentafluoride Generation and Characterization of 1-Alkoxypentafluoroallyl Cations, Journal of Fluorine Chemistry, vol. 129 (2008), pp. 1011-1017.
Pozdnyakovich et al., Fluorine-Containing Carbocations. IV. The Use of Salt Solutions of Stable Polyfluorinated α, α-Difluorobenzyl and α-Fluorodiphenylmethyl Cations in Antimony Pentafluoride in the Synthesis of Poly-Fluorinated Benzoic Acids, Benzophenones and Diphenyl-Difluoromethanes, Journal of Fluorine Chemistry, vol. 4 (1974), pp. 317-326.
Pozdnyakovich et al., Fluorine-Containing Carbocations. III. Alkylation of Polyfluorobenzenes With Poly-Fluorinated α, α-Difluorobenzyl Cations and Generation of Plyfluorinated α-Fluorodiphenylmethyl Cations, Journal of Fluorine Chemistry, vol. 4 (1974), pp. 297-316.

* cited by examiner

*Primary Examiner* — Sikarl Witherspoon

(57) ABSTRACT

This invention relates to fluoroalkyl and chlorofluoroalkyl benzenes with relatively high boiling points, having zero ozone depletion potential and low global warming potential. This invention also relates to the preparation of such fluoroalkyl and chlorofluoroalkyl benzenes. These materials can be used as reaction and heat transfer media, cleaning agents and as intermediates for biologically active materials.

5 Claims, No Drawings

FLUOROALKYL AND CHLOROFLUOROALKYL BENZENES

FIELD OF THE INVENTION

This invention relates to fluoroalkyl and chlorofluoroalkyl benzenes with relatively high boiling points, having zero ozone depletion potential and low global warming potential. This invention also relates to the preparation of such fluoroalkyl and chlorofluoroalkyl benzenes. The materials can be used as reaction and heat transfer media, cleaning agents and as intermediates for biologically active materials.

BACKGROUND

The reaction of octafluorotoluene with hexafluoropropene is known to make the perfluorinated iso-butylbenzene as shown below:

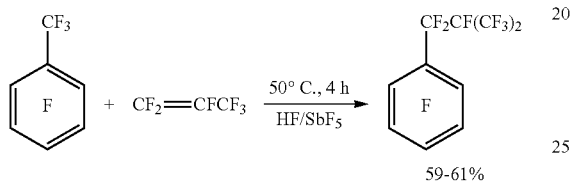

from "Syntesy Ftororganicheskich Soedinenii. Monomery I promezhutochnye porukty. Eds. I.Knunyants and G. Yakobson, Khimiay, Moskve, USSR, 1977, p. 141.

SUMMARY

One aspect of this invention is a process comprising reacting benzotrifluorides of Formula 1

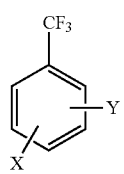

Formula 1 wherein X and Y are independently F, Cl, Br, I, $R_f$, or $OR_f$; with a fluoro-olefin selected from the group consisting of tetrafluoroethylene (TFE), $CFH=CF_2$, $CFCl=CFCl$, $CFCl=CF_2$, $CH_2=CF_2$, and $CF_2=CFCF_3$, in the presence of strong Lewis acid selected from the group consisting of antimony pentafluoride ($SbF_5$) and aluminum chlorofluoride ($AlCl_xF_y$), where x+y=3. As an illustration, when the fluoro-olefin is tetrafluoroethylene, the product comprises a fluoroalkylbenzene of Formula 2, where $R_f$ is $-CF_2CF_2CF_3$ or $-CF(C_2F_5)_2$

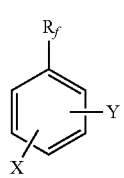

Formula 2

Another aspect of this invention is a composition comprising a fluoroalkylbenzene of Formula 2.

Another aspect of this invention is a process comprising reacting a benzotrifluoride of Formula 3 with a fluoro-olefin selected from the group consisting of TFE, $CFCl=CFCl$, and $CFCl=CF_2$ in the presence of a stoichiometric amount of aluminum chloride.

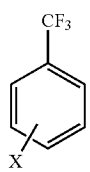

Formula 3

X=F, Cl, Br, I, $C_1$-$C_8$ alkyl, $R_f$, $-OR_f$, aryl or heteroaryl

As an illustration, one product can comprise a substituted benzene of Formula 4:

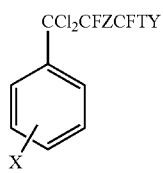

Formula 4

X=F, Cl, Br, I or $CCl_3$, and Y, Z and T=F or Cl.

Another aspect of this invention is a composition comprising a fluoroalkylbenzene of Formula 4.

Another aspect of this invention is a process comprising hydrolyzing a fluoroalkyl benzene of Formula 5 to form a fluorinated aromatic ketone of Formula 6:

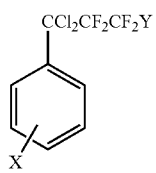

Formula 5

X=F, Cl, Br, I, $C_1$-$C_8$ alkyl, aryl, heteroaryl or $CCl_3$, and Y=F or Cl

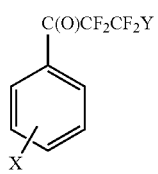

Formula 6

X=F, Cl, Br, I, $C_1$-$C_8$ alkyl, aryl, heteroaryl or C(O)OH, and Y=F or Cl.

Another aspect of this invention is a fluorinated aromatic ketone of Formula 6.

DETAILED DESCRIPTION

A process for preparing fluoroalkyl benzenes is illustrated in Scheme A:

Scheme A

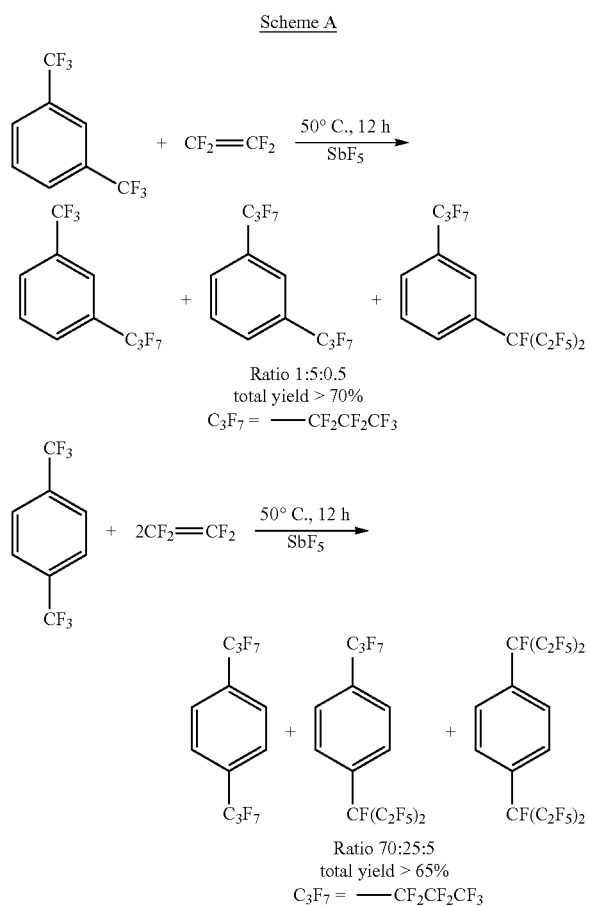

The reaction is carried out in either batch, semicontinous or continuous mode at a temperature range of −40-100° C., or preferably 0-50° C., by addition of gaseous fluoroolefin to a mixture of the corresponding benzotrifluoride and the catalyst at either atmospheric or elevated pressure 1-200 psi (tetrafluorethylene) and 1-500 psi (preferably 1-300 psi) for other fluoro-olefins. Antimony pentafluoride or aluminum chlorofluoride (ACF) can be used as catalyst at a level of 0.1 to 20 mol % ($SbF_5$) or weight % (ACF). The reaction can be carried out in the presence of inert solvent that is compatible with the catalyst and reagents. Alternatively, the starting arene (benzotrifluoride) or reaction products can be used as reaction media.

ACF can be prepared by the reaction of $CCl_3F$ with $AlCl_3$, as described in Example 1 of U.S. Pat. No. 5,157,171, incorporated herein by reference. The product, $AlCl_xF_y$, is a light-colored amorphous solid, in which x+y=3. Typically, most of the chlorine has been replaced by fluorine.

A process for preparing chlorofluoroalkyl benzenes is illustrated in Scheme B:

Scheme B

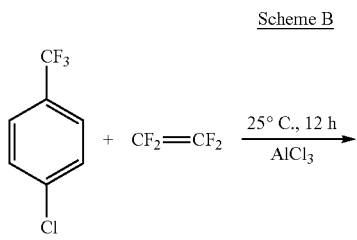

Molar ratio benzene: TFE:$AlCl_3$ = 0.5:0.5:0.3

-continued

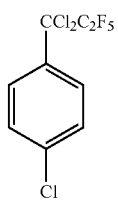

(1)
Yield ~40% @ 70% conversion; ~54% on converted

In this process, aluminum chloride serves as a catalyst and reagent, with a ratio of aluminum chloride to benzotrifluoride of 10-100 mol %, or 30-100 mol %. This reaction is carried out in either batch, semi-continuous or continuous mode at a temperature of −40-100° C., preferably 0-50° C. Gaseous fluoroolefin is added to a mixture of the corresponding benzotrifluoride and the catalyst at either atmospheric or elevated pressure: 1-200 psi for tetrafluorethylene, and 1-500 psi, preferably 1-300 psi, for other fluoro-olefins. The reaction can be carried out in the presence of an inert solvent that is compatitable with aluminum chloride and the other reagents used in the process. Suitable solvents include dichloromethane and 1,2-dichloroethane. In some embodiments, the products of the reaction can be used as reaction media.

Both routes provide access to a wide range of fluoroalkylated aromatic compounds.

A process for preparing fluorinated aromatic ketones is illustrated in Scheme C:

Scheme C

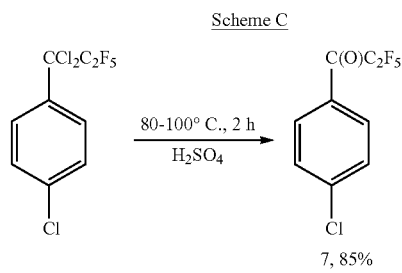

7, 85%

The reaction is carried out in either batch, semicontinous or continuous mode at a temperature range of 20 to 200° C., or preferably 60-100° C., by addition of the corresponding fluoroalkyl benzene to sulfuric acid at either atmospheric or elevated pressure 10-300 psi. The reaction can be carried out in the presence of inert solvent that is compatible with the catalyst and reagents. Alternatively, the starting fluoroalkyl benzene or reaction products can be used as reaction media.

EXAMPLES

All starting materials and solvents were obtained from commercial sources (Sigma-Aldrich, SynQuest and DuPont) and used as received, unless otherwise stated.

Example 1

Reaction of 1,3-Bis(trifluoromethyl)benzene with Tetrafluoroethylene (TFE)

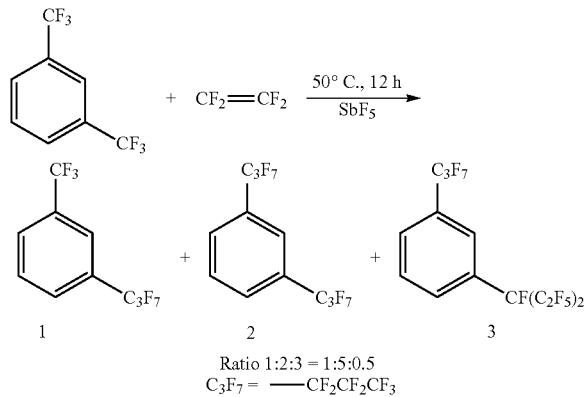

Ratio 1:2:3 = 1:5:0.5
$C_3F_7 = $ ——$CF_2CF_2CF_3$

A 400 mL shaker tube was loaded with 55 g of 1,3-bis (trifluoromethyl)benzene and 10 g of $SbF_5$. The tube was evacuated, charged with 50 g of TFE, and agitated for 12 h at 25° C. The crude product was unloaded from the shaker tube and washed with water. The organic layer was separated, dried over $MgSO_4$ and filtered to give 95 g of crude product, containing compounds 1, 2 and 3 in a ratio of 1:5:05, as determined by NMR and GC/MS. The crude product was distilled under reduced pressure (15 mm Hg) to give: 40 g of a fraction (b.p. 58-71° C.), containing mixture 1 and 2 in a ratio of 30:70; 33 g of a fraction (b.p. 71-81° C.) containing a mixture of 2 and 3 in a ratio of 80:20; and 6.5 g of a fraction (b.p. 81-88° C.) containing a mixture of 2 and 3 in a ratio of 1:1.

Compound 1. $^{19}F$ NMR ($CDCl_3$): −63.44 (3F, s), −80.40 (3F, t, 10 Hz), −112.40 (2F, q, 10 Hz), −126.66 (2F, s) ppm. $H^1$ NMR ($CDCl_3$): 7.60 (1H, d), 7.80 (3H, d) ppm.

Compound 2. $^{19}F$ NMR ($CDCl_3$): −80.44 (3F, t, 10 Hz), −112.40 (2F, q, 10 Hz), −126.66 (2F, s) ppm. $H^1$ NMR ($CDCl_3$): 7.60 (1H, d), 7.80 (3H, d) ppm.

Compound 3. $^{19}F$ NMR ($CDCl_3$): −79.65 (3F, t), −80.44 (6F), −112.56 (2F), −120.46 (4F, A:B quartet), −127.30 (2F, s), −182.96, 1F, m) ppm. $H^1$ NMR ($CDCl_3$): 7.60 (1H, d), 7.80 (3H, d) ppm.

Example 2

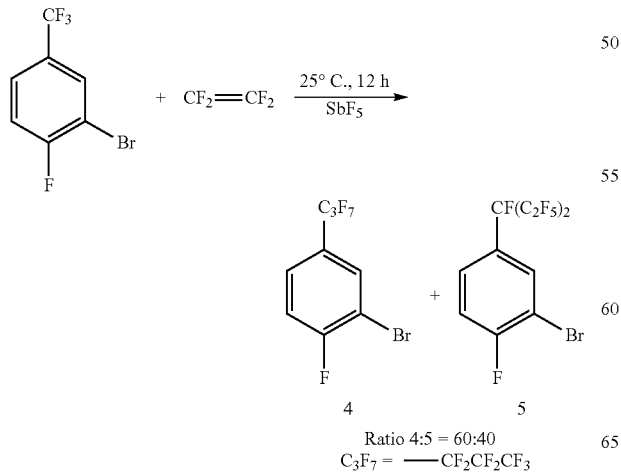

Ratio 4:5 = 60:40
$C_3F_7 = $ ——$CF_2CF_2CF_3$

A 400 mL shaker tube was loaded with 50 g of 3-bromo-4-fluorobenzotrifluoride and 10 g of $SbF_5$. The shaker tube was evacuated, charged with 20 g of TFE, and agitated for 12 h at 25° C. The crude product was unloaded from the shaker tube and washed with water. The organic layer was separated, dried over $MgSO_4$ and filtered to give 37 g of crude product, containing benzotrifluoride and compounds 4 and 5 in a ratio of 10:60:30, respectively, as determined by NMR and GC/MS. The reaction mixture was distilled at atmospheric pressure, using a spinning-band distillation column to give 15.3 g of a fraction (b.p. 142-144° C. at 760 mm Hg) and 13.5 g of residue. According to NMR analysis, the distilled fraction contained compounds 4 and 5 in a ratio of 85:15. The residue was found to be a mixture of 4 and 5 in a ratio of 30:70.

Compound 4. $^{19}F$ NMR ($CDCl_3$): −80.38 (3F, t), −101.28 (1F, m), −111.56 (2F, m), −126.61 (2F, s) ppm. $H^1$ NMR ($CDCl_3$): 7.32 (1H, m), 7.70 (1H, m), 7.92 (1H, m) ppm.

Compound 5. $^{19}F$ NMR ($CDCl_3$): −79.33 (6F, m)), −102.46 (1F, m), −120.33 (4F, A:B quartet), —181.75, 1F, m) ppm. $H^1$ NMR ($CDCl_3$): 7.32 (1H, m), 7.70 (1H, m), 7.92 (1H, m) ppm.

Example 3

Reaction of 4-Chlorobenzotrifluoride with TFE in the Presence of $AlCl_3$

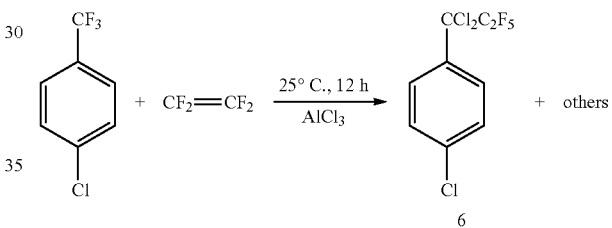

A 400 mL shaker tube was loaded with 90 g of 4-chlorobenzotrifluoride and 39 g of anhydrous $AlCl_3$ (powder). The shaker tube was evacuated, charged with 30 g of TFE, and agitated for 12 h at 25° C. The crude product was unloaded from the shaker tube and slowly added to 1 kg of crashed ice. The organic layer was separated, dried over $MgSO_4$, filtered and distilled under reduced pressure to give 60.5 g of a fraction (b.p. 155-165° C.), which was found to be compound 6 (purity 95%; 54% yield; 70% conversion of 4-chlorobenzotrifluoride).

$^{19}F$ NMR ($CDCl_3$): −79.33 (3F, s), −113.95 (2F, s) ppm. $H^1$ NMR ($CDCl_3$): 7.45 (2H, d), 7.75 (2H, d) ppm.

Example 4

Preparation of Pentafluoroethyl-4-chlorophenyl Ketone

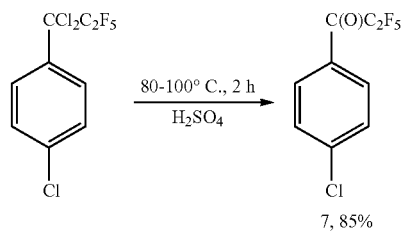

Compound 6 (8.6 g) was added to 20 ml of 96% $H_2SO_4$ and the reaction mixture was kept at 60-100° C. until evolution of HCl ceased. The product was transferred under reduced pressure into cold trap. It was analyzed by GC and NMR and found to be compound 7 (6 g, 85% yield, 99% purity).

$^{19}$F NMR (CDCl$_3$): −82.17 (3F, s), −116.25 (2F, s) ppm. $H^1$ NMR (CDCl$_3$): 7.55 (2H, d), 8.10 (2H, d) ppm.

IR(KCl, liquid film): 1710 (C=O) cm$^{-1}$.

What is claimed is:

1. A process comprising reacting benzotrifluorides of Formula 1

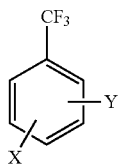

Formula 1 wherein X and Y are independently F, Cl, Br, I, $R_f$ or $OR_f$; with a fluoro-olefin selected from the group consisting of tetrafluoroethylene (TFE), CFH=CF$_2$, CFCl=CFCl, CFCl=CF$_2$, CH$_2$=CF$_2$, and CF$_2$=CFCF$_3$, in the presence of aluminum chlorofluoride.

2. A composition comprising a fluoroalkylbenzene of Formula 2

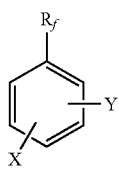

Formula 2 wherein $R_f$ is —CF$_2$CF$_2$CF$_3$ or —CF(C$_2$F$_5$)$_2$ and wherein X and Y are independently F, Cl, Br, I, $R_f$ or $OR_f$.

3. A process comprising reacting a benzotrifluoride of Formula 3

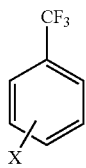

Formula 3 wherein X=F, Cl, Br, I, C$_1$-C$_8$ alkyl, $R_f$, —$OR_f$, aryl or heteroaryl;

with a fluoro-olefin selected from the group consisting of TFE, CFCl=CFCl, and CFCl=CF$_2$ in the presence of a stoichiometric amount of aluminum trichloride or AlCl$_x$F$_y$, where x+y=3.

4. A composition comprising a substituted benzene of Formula 4:

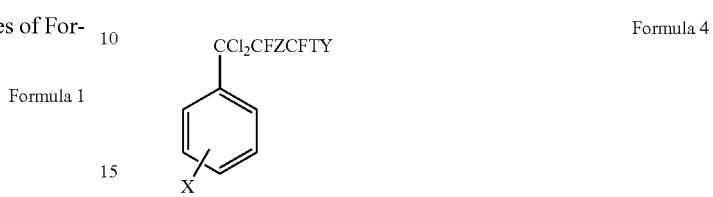

Formula 4 wherein X=F, Cl, Br, I or CCl$_3$, and Y, Z and T=F or C.

5. A process comprising hydrolyzing a fluoroalkyl benzene of Formula 5:

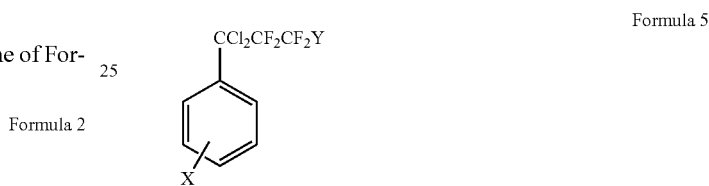

Formula 5 wherein X=F, Cl, Br, I, C$_1$-C$_8$ alkyl, aryl, heteroaryl or CCl$_3$, and Y=F or Cl, to form a fluorinated aromatic ketone of Formula 6:

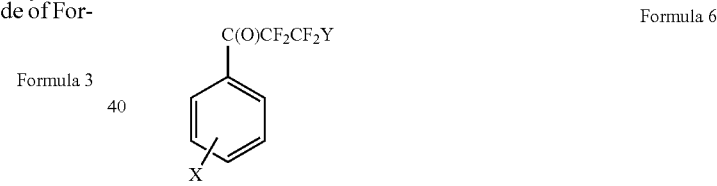

Formula 6 wherein X=F, Cl, Br, I, C$_1$-C$_8$ alkyl, aryl, heteroaryl or C(O)OH, and Y=F or Cl.

* * * * *